United States Patent
Paige et al.

(10) Patent No.: US 7,126,685 B1
(45) Date of Patent: Oct. 24, 2006

(54) OPTICAL ABSORBANCE SENSITIVITY AND RELIABILITY IMPROVEMENT VIA ROTATION OF SAMPLE CONTAINER

(75) Inventors: Mark E. Paige, Santa Fe, NM (US);
David S. Bomse, Santa Fe, NM (US);
Joel A. Silver, Santa Fe, NM (US)

(73) Assignee: Southwest Sciences incorporated, Santa Fe, NM (US)

(*) Notice: Subject to any disclaimer, the term of this patent is extended or adjusted under 35 U.S.C. 154(b) by 300 days.

(21) Appl. No.: 10/749,295

(22) Filed: Dec. 31, 2003

Related U.S. Application Data

(60) Provisional application No. 60/437,794, filed on Jan. 2, 2003.

(51) Int. Cl.
*G01J 3/02* (2006.01)
*G01J 3/42* (2006.01)

(52) U.S. Cl. .............. 356/326; 356/246; 356/427
(58) Field of Classification Search ........ 356/319, 356/326, 328
See application file for complete search history.

(56) References Cited

U.S. PATENT DOCUMENTS

| | | |
|---|---|---|
| 3,830,969 A | 8/1974 | Hofstein |
| 3,966,332 A | 6/1976 | Knapp |
| 4,372,683 A | 2/1983 | Sternberg |
| 4,684,258 A | 8/1987 | Webster |
| 5,155,019 A | 10/1992 | Sussman et al. |
| 5,267,019 A | 11/1993 | Whittaker |
| 5,386,287 A * | 1/1995 | Berssen et al. ............ 356/326 |
| 5,416,075 A * | 5/1995 | Carson et al. ............ 514/23 |
| 5,473,161 A | 12/1995 | Nix et al. |
| 5,482,842 A | 1/1996 | Berndt |
| 5,523,560 A | 6/1996 | Manique et al. |
| 5,614,718 A | 3/1997 | Bace |
| 5,694,221 A | 12/1997 | Knapp |
| 6,639,678 B1 | 10/2003 | Veale |
| 6,785,433 B1 * | 8/2004 | Tiefenthaler ............ 385/12 |

FOREIGN PATENT DOCUMENTS

| | | | |
|---|---|---|---|
| JP | 7-55697 | * | 3/1995 |
| WO | WO 02/12865 A1 | * | 2/2002 |

OTHER PUBLICATIONS

Templeton, A.C., "Rapid Headspace Oxygen Analysis for Pharmaceutical Packaging Applications," *Pharmaceutical Technology*, pp. 44-61(Jul. 2002).

* cited by examiner

*Primary Examiner*—F. L. Evans
(74) *Attorney, Agent, or Firm*—Jeffrey D. Myers; Peacock Myers, P.C.

(57) ABSTRACT

An absorption spectroscopy method comprising providing a sample in a container, rotating the container, while rotating the container, directing a beam of electromagnetic radiation through the container, the beam comprising one or more wavelengths selected from the group consisting of visible wavelengths, infrared wavelengths, and ultraviolet wavelengths, and measuring characteristics of the beam after it passes through the container. Also an absorption spectroscopy apparatus comprising a container holder, a drive rotating the container holder, means for, while rotating the container, directing a beam of electromagnetic radiation through the container, the beam comprising one or more wavelengths selected from visible wavelengths, infrared wavelengths, and ultraviolet wavelengths, and means for receiving the beam after passage through the container.

18 Claims, 3 Drawing Sheets

OPTICAL ABSORBANCE SENSITIVITY AND RELIABILITY IMPROVEMENT VIA ROTATION OF SAMPLE CONTAINER

CROSS-REFERENCE TO RELATED APPLICATIONS

This application claims the benefit of the filing of U.S. Provisional Patent Application Ser. No. 60/437,794, entitled "Improvement of Optical Absorbance Sensitivity and Reliability Through Bottle Spinning", filed on Jan. 2, 2003, and the specification thereof is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DMI 0109371 and Grant No. DMI0215797 awarded by the U.S. National Science Foundation.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to the fields of optical absorption spectroscopy and analytical chemistry.

2. Description of Related Art

Absorption of light by a chemical species inside a cell is a commonly employed method to measure the concentration of the species. The absorbance, A, which is defined as the logarithmic ratio of the incident light intensity, $I_0$, to that transmitted through the sample, I, can be related to the absorbing species' concentration, c, using Beer's law:

$$A = \text{Log}(I_0/I) = \sigma c \, l$$

where $\sigma$ is the cross section or extinction coefficient and l is the optical path length through the sample. Other materials in the optical beam path that decrease the transmitted beam intensity may limit the sensitivity to the species of interest.

One manner in which absorbance sensitivity for a particular species is commonly reduced is through the presence of optically scattering surfaces in the light path. When a light beam travels through a transparent material such as a window, back reflections and beam scattering occur. When light that has been scattered by one surface is again back-scattered forward along the original beam path by a second surface, an optical cavity or etalon has been formed. If the light from this etalon reaches the detector, a reduction in the light intensity may be observed. This intensity reduction arises from destructive interference between the incident and reflected light beams. Interference occurs when the refractive index weighted length of the etalon is not exactly a half integer multiple of the light wavelength. In such a state, a non-resonant cavity exists. As the wavelength of the light is varied—perhaps to measure a spectrum—the etalon may periodically become resonant. Thus, the magnitude of the interference observed in a wavelength scan will oscillate, creating a periodically undulating background.

The overlapping reflections and scattering causing interferences can originate from the different surfaces of one transparent object or between the surfaces of different transparent objects. These interferences change the transmitted beam intensity and thus, change the overall absorbance. In high sensitivity absorption spectroscopy measurements, absorbances below 1 part in $10^5$ can be measured. Frequently, the baseline oscillations created by interferences limit the minimum absorbance that can be attributed to the species being detected. Minimizing and/or eliminating these interferences is essential for increasing the measurement sensitivity to the species being detected.

When a bottle (container) is placed in the beam path, interferences from back reflections and beam scatter are caused by the bottle's walls. The magnitude of these interferences varies with the optical clarity of the bottle at the probe wavelength. The optical clarity of the bottle is determined by the bottle wall material as well as any material that is adhering to the bottle wall, either internally or externally. Due to variation in optical clarity across the bottle, some regions of the bottle wall will generate smaller interferences than others. In addition, the magnitude of the interference at a given wavelength is determined by the refractive index weighted distance between the reflecting/scattering surfaces. In the case where the inner and outer surfaces of a given bottle wall are causing the interference, the thickness of the wall is a factor in the magnitude of the interference at a specific wavelength.

Reducing the presence of interferences in optical systems has been the subject of many studies reported in the absorption spectroscopy literature. As noted below in the review of relevant patents, a variety of approaches have been tried. These approaches involve post measurement signal processing, varying the wavelength bandwidth of the light source, adding optical elements to the beam path, or mechanically moving parts of the optical system in order to reduce the signals caused by the interferences.

Aside from interference fringes, another problem encountered with performing absorbance measurements through containers is the presence of opaque materials adhering to the container walls either internally or externally in a non-uniform manner. For example, in a bottle containing liquid where headspace gas concentration is being monitored, spots or droplets of material may form on the container wall above the fill level. On the exterior of the bottle, miscellaneous material may exist. In addition, scratches may be present on the bottle. If the optical beam should be incident on these less transparent regions, greatly reduced or no light may reach the detector. The reduced signal level can be problematic in terms of reducing signal to noise levels or in terms of gain linearity. With low signal levels, electronic noise may become significant. For single wavelength measurements, the additional loss of intensity caused by spurious material will increase the observed absorbance. This added absorbance cannot be separated from that being generated by the species of interest inside the container. Thus, methods that eliminate or reduce absorbances from material other than the species being measured will increase the measurement sensitivity.

The following patents that address fringe reduction in optical absorption measurements do not teach the present invention or its advantages:

Silver and Stanton, "Laser Absorption Detection Enhancing Apparatus and Method", U.S. Pat. No. 4,934,816, describe a method for improving optical absorption sensitivity by longitudinally vibrating an element of the optical system along the beam direction. The vibrating element must be contained within the etalon and cause the length of the optical cavity to oscillate by more than one quarter of the optical wavelength and preferable several wavelengths. The oscillation averages the magnitude of the interference over all phases of the incident beam. This averaging serves to reduce the sensitivity of the interference magnitude to slight changes in the etalon path length. It also eliminates the wavelength dependence of the interference. The result is that periodic oscillations caused by an etalon in a wavelength spectrum are greatly reduced. The present invention does not utilize a longitudinal vibrational motion of an optical element in the system, but rather utilizes variations in the bottle wall thickness and optical clarity to eliminate the interferences. The bottle does not translate with the present invention, but rather rotates.

James R. Veale, "Apparatus and method for nondestructive monitoring of gases in sealed containers", U.S. Pat. No. 6,639,678, describes a system and method for measuring a gas inside a sealed container using absorption spectroscopy. A diverging beam is used in order to reduce scattering overlap with the incident beam and thus, reduce the interferences present in the measurement. The present invention does not put any requirement on the beam spatial characteristics.

Christopher R. Webster, "Method and apparatus for enhancing laser absorption sensitivity", U.S. Pat. No. 4,684,258, uses an oscillating plate placed at Brewster's angle inside the interfering etalon to spoil the cavity. The plate is angularly dithered approximately 1 degree in order to oscillate the etalon path length. A problem with this method is that the plate will introduce new interferences in the system. The present invention does not utilize an optic placed at Brewster's angle or any additional optical components to spoil the etalon.

Klaus W. Berndt, "Methods for detecting microorganisms in blood culture vials", U.S. Pat. No. 5,482,842, describes a method of measuring carbon dioxide in vials. A dual beam approach is taken in order to eliminate background effects from the vial walls. While this patent does not explicitly address interference fringes, it is concerned with background effects. This method does not utilize mechanical motion as a means of reducing background noise.

Whittaker et al., "Method and apparatus for reducing fringe interference in laser spectroscopy", U.S. Pat. No. 5,267,019, describe a method for reducing fringes by modifying the wavelength bandwidth of the light source. This method utilizes a triangular wavelength modulation on the laser. The triangular waveform enhances the species signal relative to that caused by interferences. This method does not utilize mechanical motion as a means of reducing interferences.

The following patents that address performing measurements inside bottles are not concerned with reducing intensity interferences due to scattering or back reflections or with reducing absorbances caused by materials that are not the species being measured.

Sussman et al., "Detection of the presence of biological activity in a sealed container utilizing infrared analysis of carbon dioxide and apparatus therefor", U.S. Pat. No. 5,155,019, describe a method and apparatus for measuring carbon dioxide in a bottle through absorption spectroscopy at 2300–2400 wave numbers. No method of reducing potential optical interference is employed by their invention.

Nix et al., "Method for testing carbonation loss from beverage bottles using IR spectroscopy", U.S. Pat. No. 5,473,161, describe measuring carbon dioxide levels inside a bottle through infrared absorption spectroscopy at 4922 to 5034 wave numbers. Again, no method of reducing potential optical interference is employed by their invention.

Sternberg et al., "Photometer with Rotating Sample Container", U.S. Pat. No. 4,372,683, disclose an improvement for light scattering type of measurements, including other scattering techniques such as fluorescence, luminescence, and scintillation. The disclosure does not relate to absorption spectroscopy, and so Sternberg et al. are not addressing etalon fringe issues or even seemingly transmission of the incident light through the bottle. Sternberg et al. are merely concerned with the background light scatter from the bottle that arrives at the detector and the attenuation of the scattered light from the sample.

Other arguably related inventions include Julius Z. Knapp, "Particle Detection Method for Detection of Contaminating Particles in Sealed Containers", U.S. Pat. No. 5,694,221; John G. Brace, "Apparatus and Method for Noninvasive Assessment of Pressurized Container Properties", U.S. Pat. No. 5,614,718; Manique et al., "Method and Apparatus for Inspecting Liquid-Filled Containers", U.S. Pat. No. 5,523,560; Knapp et al., "Method and Apparatus for Inspecting Liquids in Transparent Containers", U.S. Pat. No. 3,966,332; and Steven R. Hofstein, "System for Detecting Particulate Matter", U.S. Pat. No. 3,830,969.

BRIEF SUMMARY OF THE INVENTION

The present invention is of an absorption spectroscopy method comprising: providing a sample in a container; rotating the container; while rotating the container, directing a beam of electromagnetic radiation through the container, the beam comprising one or more wavelengths selected from the group consisting of visible wavelengths, infrared wavelengths, and ultraviolet wavelengths; and measuring characteristics of the beam after it passes through the container. In the preferred embodiment, the sample is in a bottle, reduction is accomplished in one or both of wavelength dependence of interference and amplitude variation of interference, and absorbance sensitivity is increased. Rotating may be in a single direction or in a plurality of directions (such as a primary and a reverse direction, optionally with direction periodically reversed). The method may additionally comprise determining a region of the container through which desired beam characteristics are optimized, whereupon rotation may be stopped so that the beam passes through the determined region. The stop may be complete or may involve rotating the container such that the beam always passes through the determined region. Rotating in most instances preferably comprises rotating through a plurality of revolutions. Directing may comprise directing a beam comprising one or more wavelengths. The method preferably additionally comprises averaging a plurality of spectra collected in the measuring step.

The present invention is also of an absorption spectroscopy apparatus comprising: a container holder; a drive rotating the container holder; means for, while rotating the container, directing a beam of electromagnetic radiation through the container, the beam comprising one or more wavelengths selected from visible wavelengths, infrared wavelengths, and ultraviolet wavelengths; and means for receiving the beam after passage through the container. In the preferred embodiment, the container holder comprises a bottle holder. Means for subsequently stopping the drive may be employed so that the beam passes through a particular region of the container. The directing means is preferably a laser, most preferably a diode laser.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is a method for improving the reliability and sensitivity of optical absorption spectroscopy measurements for chemical species inside a bottle or container. The improvement is implemented by rotating (spinning) the bottle during the optical absorption measurement.

Figure 1:
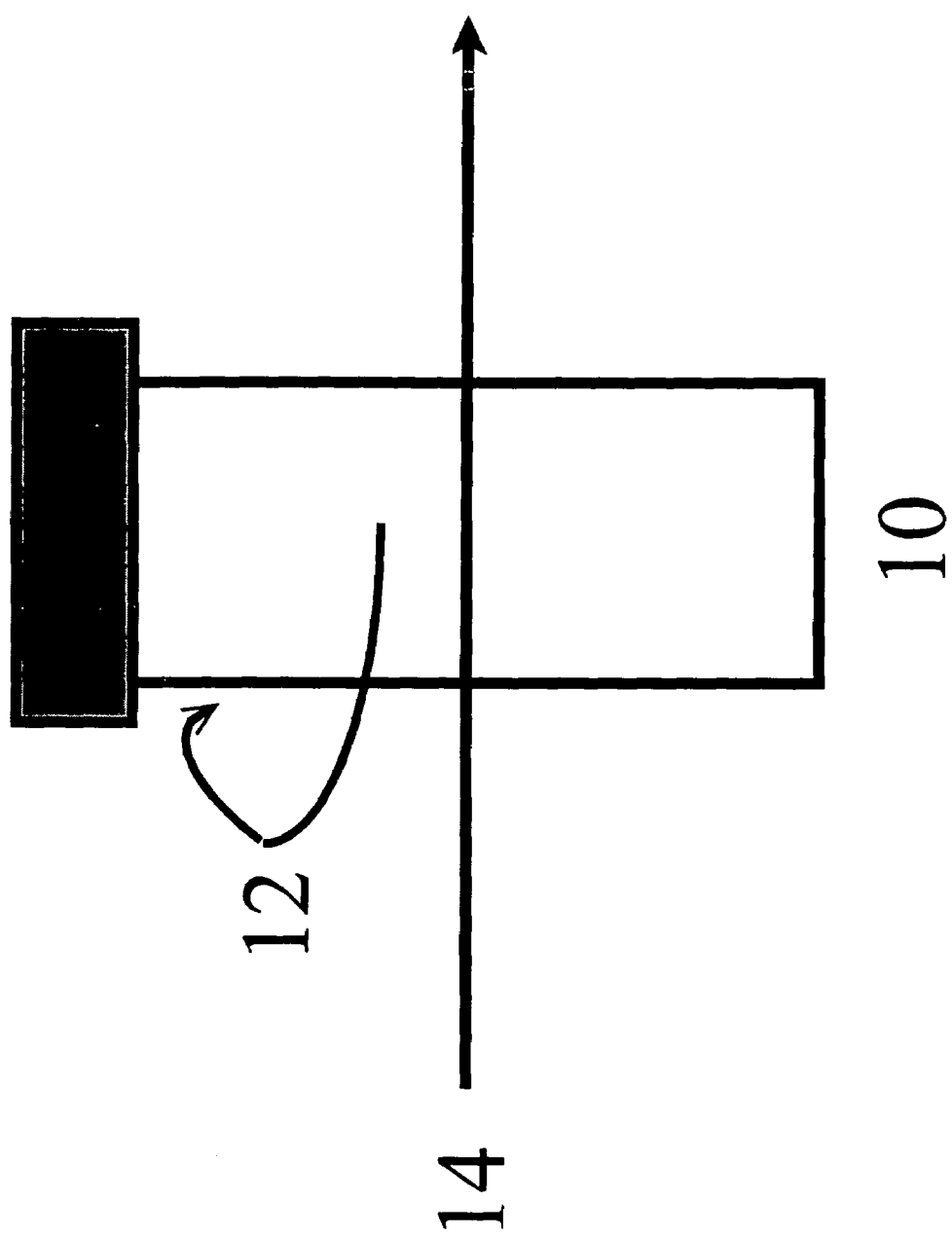
FIG. 1 is a schematic drawing illustrating the bottle rotation method of the invention used to improve absorption measurements.

As shown in FIG. 1, the invention is implemented by rotating 12 the bottle 10 during the optical absorption measurement. By rotating the bottle, the electromagnetic radiation beam 14 (preferably optical, infrared, and/or ultraviolet) is exposed to regions of varying optical clarity and bottle wall thickness. Regions of higher and lesser interference and optical transparency will be probed. If the bottle were arbitrarily placed in the beam path but not rotated, a high interference or opaque region might be probed exclusively. Thus, by rotating the bottle, the average reliability of the measurement is improved. This is particularly so when the rotation is of at least one or more complete rotations, but a lesser degree of rotation is also beneficial.

In addition, because the wall thickness of a given bottle typically varies by more than a quarter of an optical wavelength, the magnitude of the interference will vary as the bottle rotates. The rotation will average the magnitude of the interferences. This averaging will greatly reduce the wavelength dependence of the interference. The averaged spectrum observed over different bottle wall regions will show vastly diminished interference oscillations. The interfering oscillations from specific points on the bottle cancel each other. With a smoother, less oscillatory background in the spectrum, a smaller species absorbance can be measured.

Figure 2:
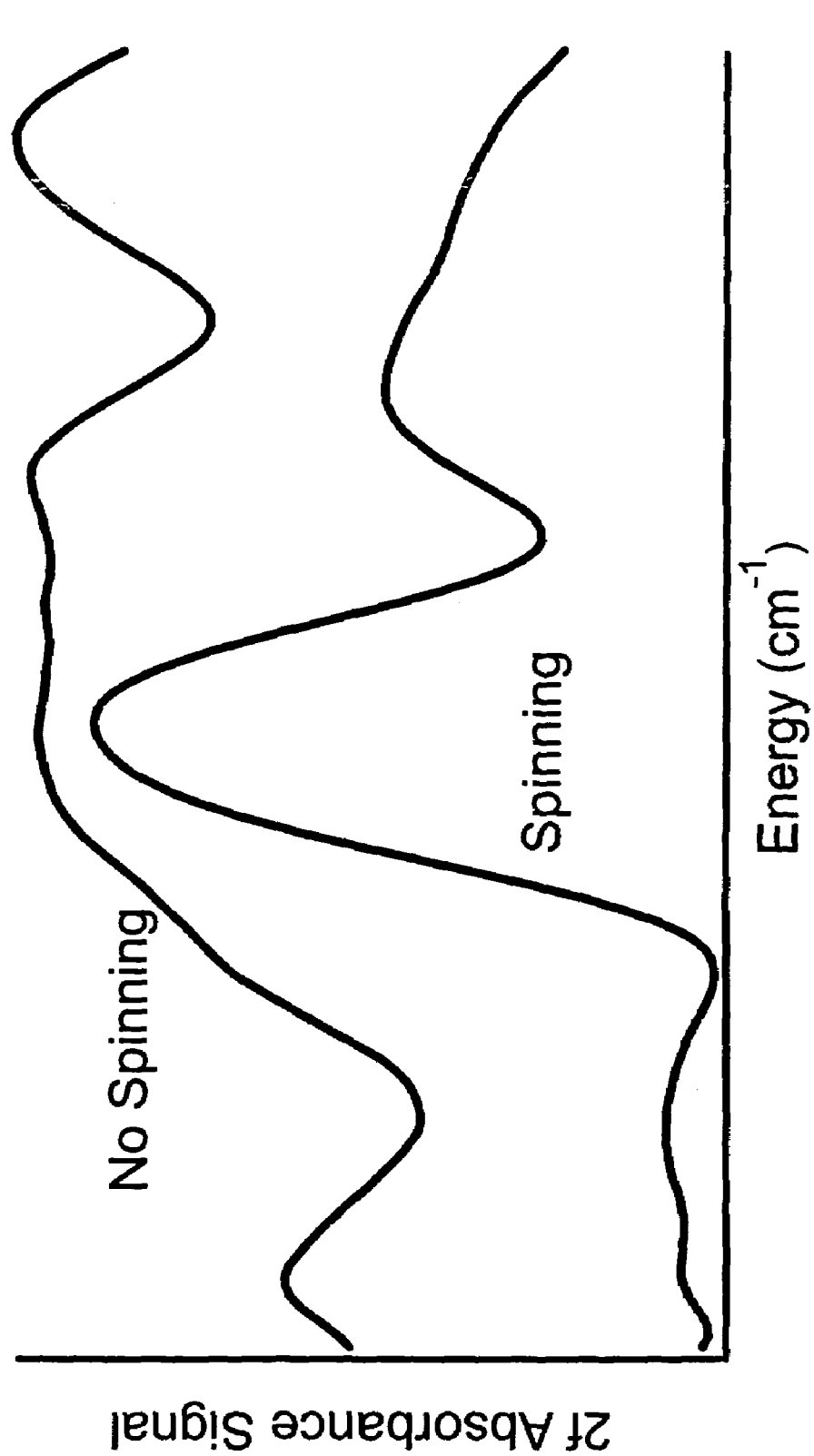
FIG. 2 is a graph of the second harmonic wavelength modulation absorption spectra taken with a bottle spinning versus not spinning; the species being measured is 2.1% gaseous oxygen inside a 17 mm diameter bottle; the absorption peak is evident when the bottle spins during the measurement and hidden in the baseline when the bottle is not rotated.

FIG. 2 shows an example of the decreased absorbance interference and increased absorbance sensitivity that results by spinning a 17 mm diameter pharmaceutical bottle during the absorbance measurement.

To implement the present invention, the bottle (container) is rotated during the absorption measurement. This rotation may be performed continuously in a single direction or it may be accomplished by occasionally or periodically reversing direction of the rotation. This motion will improve the reliability and sensitivity of the measurement. During the rotation of the bottle, a favorable region of the bottle for making the absorption measurement may be located. For example, the optimal region may be where the transmitted beam intensity is maximized or where the flattest absorption background is found. Measurement reliability and sensitivity can also be improved by limiting the angular movement of the bottle so that the optical beam probes only this region of the bottle. The bottle should be rotated during the measurement to reduce interferences, but with frequent reversal in rotation direction.

In any of these embodiments, there must preferably be averaging of the spectral measurements over the full range of the bottle surface that is being probed. Thus, for a multipoint spectrum, entire spectra might be measured rapidly with respect to the bottle motion and averaged or conversely, a slow, single spectral sweep could be made with the bottle rotation occurring at much higher frequency.

Figure 3:
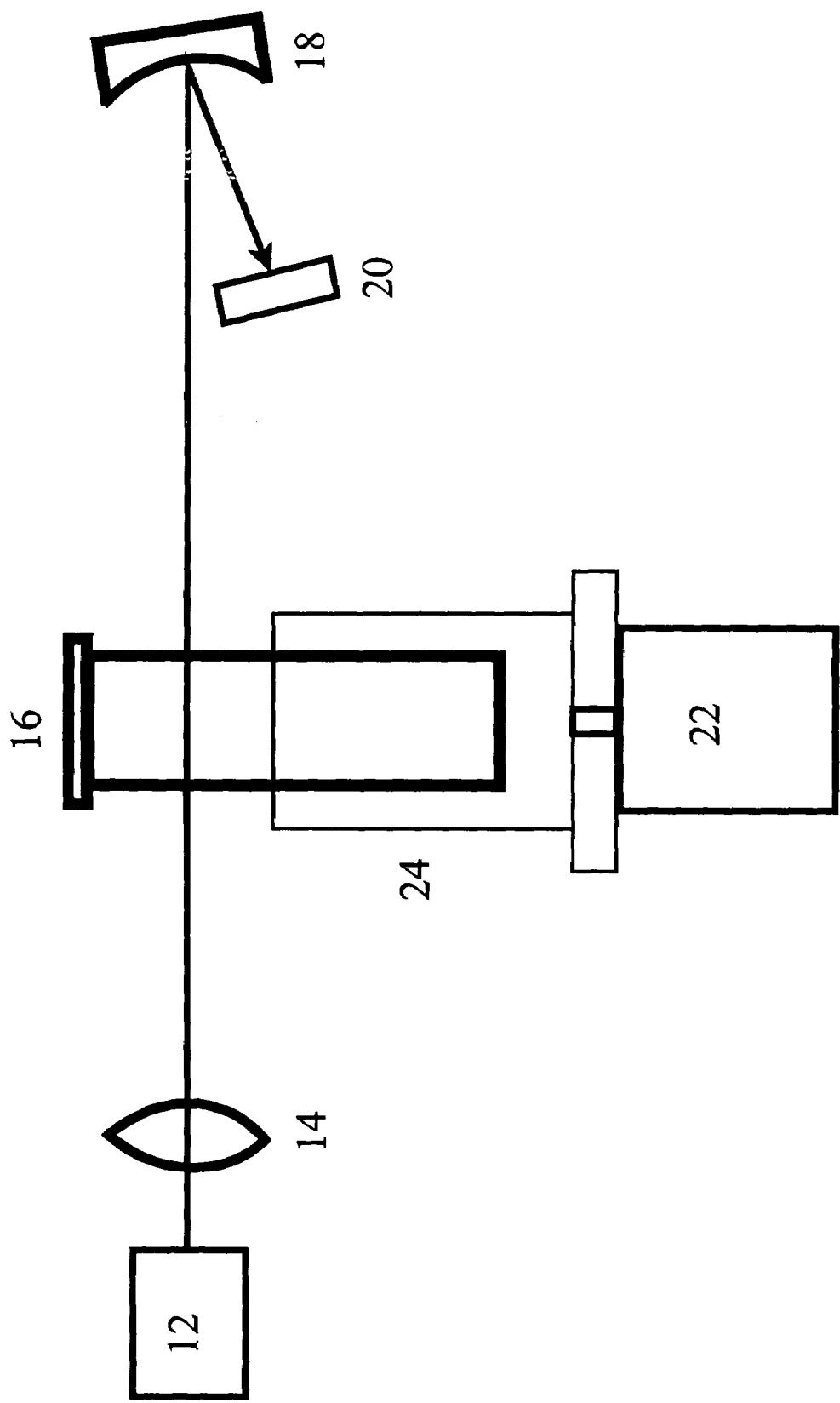
FIG. 3 is a block diagram of the preferred apparatus of the invention.

The preferred apparatus 10 according to the invention is shown in FIG. 3. Laser (or like beam directing means) 12, preferably a diode laser, emits coherent light through collimating lens 14, which then passes through bottle 16 containing a sample under study, and thence to focusing mirror 18 and detector (or like receiving means) 20. While the light is emitted, the bottle is spun via a drive (preferably a spinning motor) 22 attached to bottle holder 24.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An absorption spectroscopy method comprising the steps of:
    providing a sample in a container;
    rotating the container;
    while rotating the container, directing a beam of electromagnetic radiation through the container, the beam comprising one or more wavelengths selected from the group consisting of visible wavelengths, infrared wavelengths, and ultraviolet wavelengths;
    measuring characteristics of the beam after it passes through the container, the measuring step comprising collecting a plurality of spectra and averaging the plurality of spectra.

2. The method of claim 1 wherein the providing step comprises providing a sample in a bottle.

3. The method of claim 1 wherein a reduction is accomplished in one or both of wavelength dependence of interference and amplitude variation of interference.

4. The method of claim 1 wherein absorbance sensitivity is increased.

5. The method of claim 1 wherein rotating comprises rotating in a single direction.

6. The method of claim 1 wherein rotating comprises rotating in a plurality of directions.

7. The method of claim 6 wherein rotating comprises rotating in a primary and a reverse direction.

8. The method of claim 7 wherein rotating comprises periodically reversing direction.

9. The method of claim 1 additionally comprising the step of determining a region of the container through which desired beam characteristics are optimized.

10. The method of claim 9 additionally comprising the step of stopping rotating of the container so that the beam passes through the determined region.

11. The method of claim 10 wherein the stopping step comprises stopping all rotation of the container.

12. The method of claim 10 wherein the stopping step comprises rotating the container such that the beam always passes through the determined region.

13. The method of claim 1 wherein the rotating step comprises rotating through a plurality of revolutions.

14. An absorption spectroscopy apparatus comprising:
a container holder;
a drive rotating said container holder;
means for, while rotating said container, directing a beam of electromagnetic radiation through said container, said beam comprising one or more wavelengths selected from the group consisting of visible wavelengths, infrared wavelengths, and ultraviolet wavelengths;
means for receiving said beam upon passage through said container; and
means for measuring characteristics of the beam after it passes through the container comprising means for collecting a plurality of spectra and means for averaging the plurality of spectra.

15. The apparatus of claim 14 wherein said container holder comprises a bottle holder.

16. The apparatus of claim 14 additionally comprising means for subsequently stopping said drive so that said beam passes through a particular region of said container.

17. The apparatus of claim 14 wherein said directing means comprises a laser.

18. The apparatus of claim 17 wherein said directing means comprises a diode laser.

* * * * *